US006995301B1

(12) United States Patent
Shorrosh

(10) Patent No.: US 6,995,301 B1
(45) Date of Patent: Feb. 7, 2006

(54) PLANT ACYLTRANSFERASES

(75) Inventor: Basil S. Shorrosh, Ft. Collins, CO (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 09/565,620

(22) Filed: May 4, 2000

Related U.S. Application Data

(60) Provisional application No. 60/132,417, filed on May 4, 1999.

(51) Int. Cl.
*A01N 5/00* (2006.01)
*C12N 15/82* (2006.01)

(52) U.S. Cl. .................. 800/298; 800/281; 435/320.1; 536/23.1

(58) Field of Classification Search ............... 536/23.1, 536/23.2, 23.6; 800/69.1, 320.1, 298, 281; 435/320.1
See application file for complete search history.

(56) References Cited

U.S. PATENT DOCUMENTS

| | | | |
|---|---|---|---|
| 5,188,958 A | 2/1993 | Moloney et al. | |
| 5,204,253 A | 4/1993 | Sanford et al. | |
| 5,254,678 A | 10/1993 | Haseloff et al. | |
| 5,356,799 A | 10/1994 | Fabijanski et al. | |
| 5,451,514 A | 9/1995 | Boudet et al. | |
| 5,453,566 A | 9/1995 | Shewmaker et al. | |
| 5,530,192 A | 6/1996 | Murase et al. | |
| 6,100,077 A | 8/2000 | Sturley et al. | |

FOREIGN PATENT DOCUMENTS

| | | |
|---|---|---|
| WO | WO 94/11516 | 5/1994 |
| WO | WO 98/36083 | 8/1998 |
| WO | WO 98/55631 | 12/1998 |
| WO | WO 98/55632 | 12/1998 |
| WO | WO 99/43202 | 9/1999 |
| WO | WO 99/63096 | 12/1999 |
| WO | WO 99/67268 | 12/1999 |
| WO | WO 99/67403 | 12/1999 |
| WO | WO 00/01713 | 1/2000 |
| WO | WO 00/07430 | 2/2000 |
| WO | WO 00/32756 | 6/2000 |
| WO | WO 00/32793 | 6/2000 |
| WO | WO 00/36114 | 6/2000 |

OTHER PUBLICATIONS

Angenon et al., "Antibiotic Resistance Markers for Plant Transformation," *Plant Molecular Biology Manual*, 1994, C1:1-13.
Brigham, "Caster: Return of an Old Crop," *New Crops*, 1993, pp. 380-383.
Cases et al., *Proc. Natl. Acad. Sci. USA*. 1998, 95:13018-13023.
Cases et al., *J. Biol. Chem.*, 1998, 273(41):26755-26764.
de Feyter et al., *Methods in Molecular Biology*, 1997, vol. 74, Chapter 43, pp. 403-415.
Hobbs et al., *FEBS Letters*, 1999, 452:145-149.
Nykiforuk et al., *Plant Physiol.*, 1999, 120(4):1207.
Perriman et al., *Proc. Natl. Acad. Sci. USA*. 1995, 92(13): 6175-6179.
Töpfer et al., *Science*, 1995, 268:681-686.
Weising et al., *Annu. Rev. Genet.*, 1998, 22:421-477.
Zou et al., *Plant Journal*, 1999, 19(6):645-653.
Frentzen, *Fett/Lipid*, 1998, 100(4-5):161-166.
Hills et al. *Biochemical Society Transactions*, 1999, 27(3): A124; Abstract #125.
Katavic et al., *Plant Physiol.*, 1995, 108:399-409.
Little et al., *Biochem. J.*, 1994, 304:951-958.
Nykiforuk et al., *Plant Physiol.*, 1999, 121:1057.
Weselake et al., *Physiol. Biochem. Mol. Biology of Plant Lipids*:1997, pp. 357-359.
Wilson et al., *Seed Oils for the Future*, 1992, Chapter 12, pp. 116-135.
GenBank Accession No. AA042298.
GenBank Accession No. AC003058.
GenBank Accession No. AC005917.
GenBank Accession No. AF051849.
GenBank Accession No. AF155224.
GenBank Accession No. AF164434.
GenBank Accession No. AF251794.
GenBank Accession No. AJ131831.

*Primary Examiner*—Elizabeth F. McElwain
(74) *Attorney, Agent, or Firm*—Fish & Richardson P.C., P.A.

(57) ABSTRACT

A gene encoding diacylglycerol acyltransferase from *Brassica napus* is described, as well as methods of altering oil content in plants using the diacylglycerol acyltransferase.

12 Claims, 2 Drawing Sheets

PLANT ACYLTRANSFERASES

This application claims priority from U.S. Provisional Application Serial No. 60/132,417, filed May 4, 1999.

TECHNICAL FIELD

The invention relates to alteration of oil content in plants.

BACKGROUND

Triacylglycerols produced in plant tissues (e.g., canola seeds) are a significant source of fatty acids in the human diet. Diets rich in animal fat appear to promote maladies such as heart disease in humans. The ability to modulate triacylglycerol synthesis in plants could allow for production of fatty acid compositions that are more beneficial for humans or more efficiently synthesized by the plant. Cloning and characterization of plant genes encoding enzymes involved in triacylglycerol synthesis and metabolism represents a major advance toward controlling triacylglycerol synthesis in plants.

SUMMARY

A new plant acyltransferase gene from *Brassica napus* has been cloned and characterized. The protein encoded by this gene is involved in triacylglycerol synthesis. Partial DNA sequences of the *B. napus* gene confirm that it is related to an *Arabidopsis thaliana* putative acyltransferase gene. Antisense expression of the *B. napus* sequence decreases total oil content.

In one aspect, the invention features an isolated nucleic acid having at least 80% (e.g., 85%, 90%, or 99%) sequence identity to the nucleotide sequence of SEQ ID NO:3, or to a fragment of the nucleotide sequence of SEQ ID NO:3, the fragment being at least 15 nucleotides in length. An isolated nucleic acid having at least 80% (e.g., 85%, 90%, or 99%) sequence identity to the nucleotide sequence of SEQ ID NO:4, or to a fragment of the nucleotide sequence of SEQ ID NO:4, the fragment being at least 15 nucleotides in length is also featured.

In another aspect, the invention features an isolated nucleic acid that includes a first and second region, the first region having at least 80% sequence identity to the nucleotide sequence of SEQ ID NO:3 and the second region having at least 80% sequence identity to the nucleotide sequence of SEQ ID NO:4. The nucleic acid can encode a diacylglycerol acyltransferase polypeptide. The first and second regions can be separated by approximately 600 nucleotides. The nucleic acid can be the insert of pMB143. An expression vector including the nucleic acid operably linked to an expression control element also is featured. The nucleic acid can be operably linked in antisense orientation.

In another aspect, the invention features a transgenic plant and progeny thereof that include an exogenous nucleic acid encoding a diacylglycerol acyltransferase polypeptide operably linked to a regulatory element, and seed produced by such plants. The nucleic acid can include a first and second region, the first region having at least 80% sequence identity to the nucleotide sequence of SEQ ID NO:3, the second region having at least 80% sequence identity to the nucleotide sequence of SEQ ID NO:4. The transgenic plant can produce seeds that exhibit a statistically significantly altered oil content as compared to seeds produced by a corresponding plant lacking the nucleic acid encoding the diacylglycerol acyltransferase polypeptide. The plant can be a soybean plant or a *Brassica* plant.

The invention also features a nucleic acid that includes the nucleotide sequence of SEQ ID NO:3 or SEQ ID NO:4 or the nucleotide sequence exactly complementary to SEQ ID NO:3 or SEQ ID NO:4. The nucleic acid also can include the RNA equivalent of the nucleotide sequence of SEQ ID NO:3 or SEQ ID NO:4, or an RNA equivalent that is exactly complementary to the nucleotide sequence of SEQ ID NO:3 or SEQ ID NO:4. The nucleotide sequences of SEQ ID NO:3 and SEQ ID NO:4 are partial sequences of the new *B. napus* gene.

In another aspect, the invention features a nucleic acid that (1) hybridizes under stringent conditions to a DNA molecule consisting of the nucleotide sequence of SEQ ID NO:3 or SEQ ID NO:4, and (2) encodes a plant acyltransferase. In addition, the invention includes a nucleic acid (1) having a nucleotide sequence which is at least 80% (e.g., at least 82, 85, 90, 92, 95, 98, or 99%) identical to the nucleotide sequence of SEQ ID NO:3 or SEQ ID NO:4, and (2) encoding a plant acyltransferase. As used herein, the term "stringent conditions" means hybridization at 42° C. in the presence of 50% formamide; a first wash at 65° C. with 2×SSC containing 1% SDS; followed by a second wash at 65° C. with 0.1×SSC.

The nucleotide sequence fragments described below can be used to hybridize against cDNA or genomic DNA libraries from a variety of sources to clone genes related to the *B. napus* acyltransferase gene. In addition, the sequence fragments can be used to design additional primers for further sequencing of the *B. napus* gene or for PCR amplification of portions of the *B. napus* gene.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
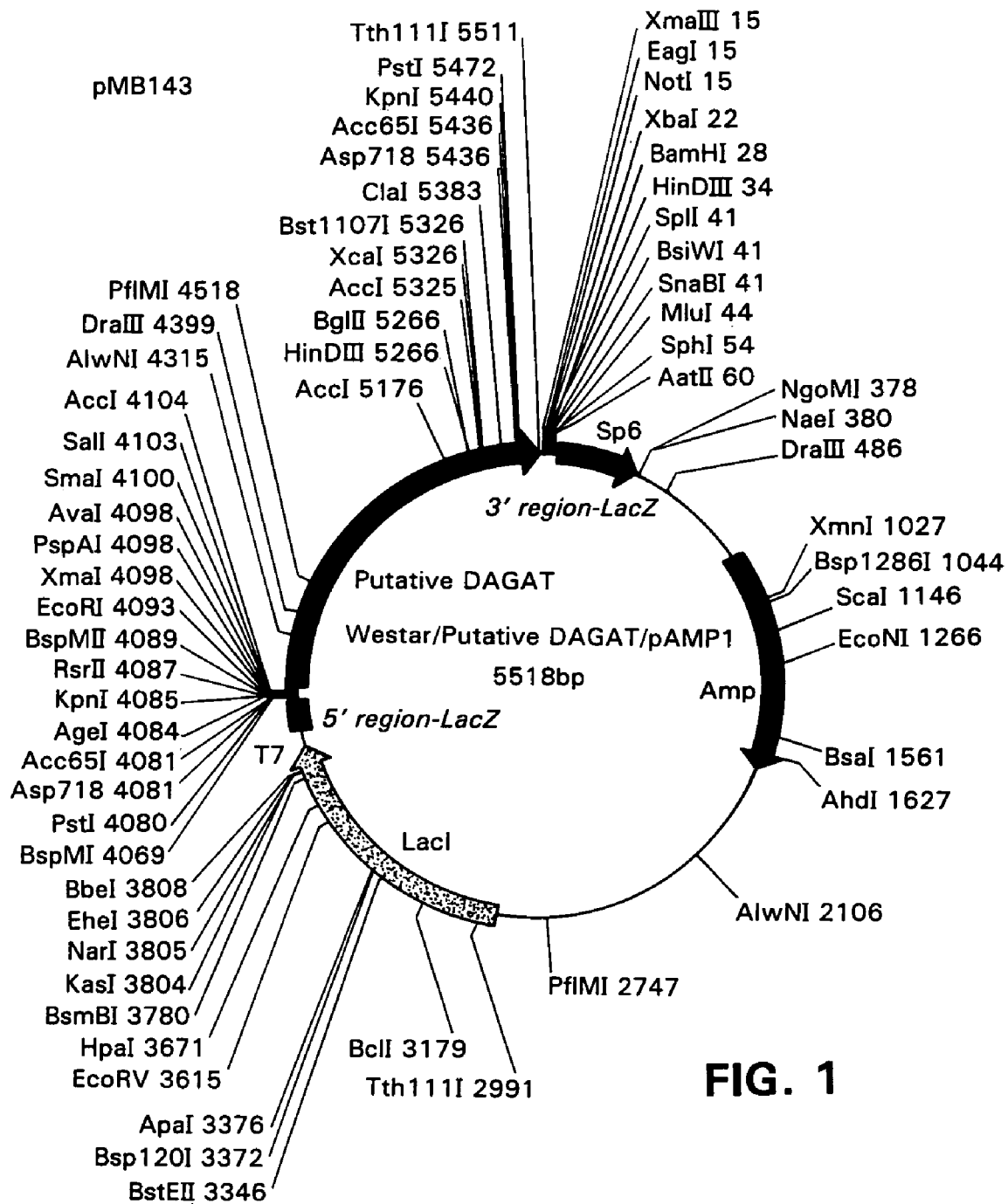
FIG. 1 is a schematic of a construct containing the acyltransferase. Restriction sites are marked.

Triacylglycerols (TAGs) are synthesized by the sequential transfer of acyl chains to the glycerol backbone by a series of enzymes in the Kennedy pathway (glycerol-3-phosphate acyltransferase, lysophosphatidic acid acyltransferase, and diacylglycerol acyltransferase). See, Töpfer et al., *Science*, 1995, 268:681–686. Diacylglycerol can be used to form TAGs or membrane glycerolipids, and is the substrate for diacylglycerol acyltransferase (DAGAT, E.C. 2.3.1.20). DAGAT transfers a third acyl chain to diacylglycerol, forming a TAG, and is the only enzyme unique to TAG synthesis in the Kennedy pathway. Thus, the reaction catalyzed by DAGAT represents a key branchpoint in TAG synthesis. As described herein, a 1.4 kB gene that encodes diacylglycerol acyltransferase (DAGAT) has been identified from *Brassica* and can be used to alter total oil content in plants.

DAGAT Nucleic Acid Molecules

The invention features isolated nucleic acids having at least 80% sequence identity, e.g., 85%, 90%, 95%, or 99% sequence identity, to the nucleic acid of SEQ ID NO:3 or SEQ ID NO:4, or fragments of the nucleic acid of SEQ ID NO:3 or 4 that are at least about 15 nucleotides (nt) in length (e.g., at least 18, 20, 22, 24, 26, 28, or 30 nt). In one embodiment, the nucleic acid includes a first region having at least 80% sequence identity to the nucleotide sequence of SEQ ID NO:3 and a second region having at least 80% sequence identity to the nucleotide sequence of SEQ ID NO:4. The first and second regions can be separated by about 590 to about 700 nucleotides, e.g., about 600 nucleotides.

Generally, percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. The total number of aligned nucleotides refers to the number of nucleotides from SEQ ID NO:3 or NO:4 that are being aligned. Nucleic acid sequences can be aligned by the Clustal algorithm of MEGALIGN® (DNASTAR, Madison, Wis., 1997) sequence alignment software. In this method, sequences are grouped into clusters by examining the distances between all pairs. Clusters are aligned as pairs, then as groups. A gap penalty of 100 and a gap length penalty of 2 are used in the alignments.

Isolated nucleic acid molecules of the invention can be produced by standard techniques. As used herein, "isolated" refers to a sequence corresponding to part or all of a gene encoding a DAGAT polypeptide, but free of sequences that normally flank one or both sides of the wild-type gene in a plant genome. As used herein, "polypeptide" refers to a chain of least eight amino acids. An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules are at least about 15 nucleotides in length. For example, the nucleic acid molecule can be about 20 to 35, 40–50, 50–100, or greater than 150 nucleotides in length, e.g., 200–300, 300–500, 500–1000, or 1100–1500 nucleotides in length. Such fragments, whether encoding a polypeptide or not, can be used as probes, primers, and diagnostic reagents. In some embodiments, the isolated nucleic acid molecules encode a full-length DAGAT polypeptide. Nucleic acid molecules can be DNA or RNA, linear or circular, and in sense or antisense orientation. The nucleic acid molecules also can be complementary to the nucleotide sequences of SEQ ID NO:3 or SEQ ID NO:4. A nucleic acid encoding a DAGAT polypeptide may or may not contain introns within the coding sequence.

Polymerase chain reaction (PCR) techniques can be used to produce nucleic acid molecules of the invention. PCR refers to a procedure or technique in which target nucleic acids are amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in PCR Primer: A Laboratory Manual, Ed. by Dieffenbach, C. and Dveksler, G., Cold Spring Harbor Laboratory Press, 1995.

Nucleic acids encoding DAGAT polypeptides also can be produced by chemical synthesis, either as a single nucleic acid molecule or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

It should be appreciated that many different nucleic acids will encode a polypeptide having a particular DAGAT amino acid sequence. The degeneracy of the genetic code is well known in the art, i.e., many amino acids are encoded by more than one nucleotide codon. It should also be appreciated that certain amino acid substitutions can be made within polypeptide sequences without affecting the function of the polypeptide. Conservative amino acid substitutions or substitutions of similar amino acids often are tolerated without affecting polypeptide function. Similar amino acids can be those that are similar in size and/or charge properties. Similarity between amino acids has been assessed in the art. For example, Dayhoff et al. (1978) in Atlas of Protein Sequence and Structure, Vol. 5, Suppl. 3, pp. 345–352, provides frequency tables for amino acid substitutions that can be employed as a measure of amino acid similarity.

Transgenic Plants

The invention features transgenic plants that have altered total oil content, i.e., increased or decreased oil content. Suitable plant species include, for example, *Brassica* spp. such as *B. napus, B. campestris, B. juncea*, and *B. rapa* (canola-type and high erucic acid rapeseed), soybean, sunflower, castor bean, safflower, crambe, palm, coconut, corn, cottonseed, olive, peanut, flax, and sesame. Canola, soy, sunflower, and safflower plants having increased oil content are particularly useful. Table 1 provides relative percent oil and protein content on a dry weight basis (unless indicated otherwise) of suitable oilseed plants.

The present invention describes a novel method of making transgenic plants that produce seeds with a statistically significant alteration in oil content. As used herein, "statistically significant" refers to a p-value of less than 0.05, e.g., a p-value of less than 0.025 or a p-value of less than 0.01, using an appropriate measure of statistical significance, e.g., a one-tailed two sample t-test. By using this method, plants can be produced that exhibit an altered oil content in their seeds. The altered oil content is statistically significant relative to the oil content of unmodified seeds. Plants produced by the method of the present invention can produce seeds having an increase in oil of from about 1% to about 25% over the oil content in seeds produced by unmodified control plants. For example, the increase in oil content for plants described herein can be from about 2% to about 20%, from about 4% to about 15%, from about 5% to about 10%, or from about 10% to about 20%, relative to unmodified plants.

TABLE 1

Relative Percent Oil and Protein Content of Oilseed Plants

| Plant | % Oil | % Protein | Key |
|---|---|---|---|
| Soybean (*Glycine max*) | ~20 | ~40 | C |
| Rapeseed (*Brassica napus*) | 40–44 | 38–41 (oil free meal) | C; D |
| Sunflower (*Helianthus annus*) | 40 | | D |
| Castor bean (*Ricinus communis*) | 50 | | A |
| Safflower (*Carthamus tinctorius*) | 36.8–47.7 | 15.4–22.5 | D |
| Crambe (*Crambe abyssinica*) | 30–35 | ~28 | B |
| Palm (*Elaeis guineensis*) | 20 >50 | | C; per fresh fruit bunch (~20% moisture); Dried kernels |
| Coconut (*Cocos nucifera*) | 34 69 | 3.5 | D; coconut flesh (50% moisture); dried kernels |
| Maize (*Zea mays*) | 3.1–5.7 | 6–12 | C; D |
| Cottonseed (*Gossypium hirsutum*) | 25–30 | 25–30 | D; kernel |
| Olive (*Olea europaea*) | 19.6 | 1.6 | fruit (52.4% moisture) |
| Peanut (*Arachis hypogaea*) | 36–56 | 25–30 | C; (unknown moisture) |
| Flax (*Linum usitatissimum*) | 35–45 | | D; per fruit capsule (~10 seeds/fruit) |
| Sesame (*Sesamum indicum*) | 53.3–57.5 | 25–30 | D; (5–7% moisture) |

(A) Brigham RD, 1993, Castor: Return of an old crop, p 380–3. In New Crops, Janick, J & Simon, JE, eds. Wiley, NY.
(B) Grombacher et al., Cooperative Extension, Institute of Agriculture and Natural Resources, University of Nebraska-Lincoln, Crambe production, Publication G93-1126A, G1126 (Field Crops), F-17 (Misc. Crops); see also pubs@unlvm.unl.edu
(C) In Principles of Cultivar Development, 1987, Fehr, WR, ed., Macmillan Publishing Co., NY.
(D) In 5th Edition Bailey's Industrial Oil & Fat Products, Vol. 2, Edible Oil & Fat Products: Oils and Oil Seeds, 1996, Hui, YH, ed., Wiley, NY.

A plant described herein may be used as a parent to develop a plant line, or may itself be a member of a plant line, i.e., it is one of a group of plants that display little or no genetic variation between individuals for total oil content. Such lines can be created by several generations of self-pollination and selection, or vegetative propagation from a single parent using tissue or cell culture techniques known in the art. Additional means of breeding plant lines from a parent plant are known in the art.

In general, plants of the invention can be obtained by introducing at least one exogenous nucleic acid encoding a DAGAT polypeptide into plant cells. As used herein, the term "exogenous" refers to a nucleic acid that is introduced into the plant. Exogenous nucleic acids include those that naturally occur in the plant and have been introduced to provide one or more additional copies, as well as nucleic acids that do not naturally occur in the plant. Typically, a nucleic acid construct containing a nucleic acid encoding a DAGAT polypeptide is introduced into a plant cell. Seeds produced by a transgenic plant can be grown and selfed (or outcrossed and selfed) to obtain plants homozygous for the construct. Seeds can be analyzed to identify those homozygotes having the desired expression of the construct. Transgenic plants can be entered into a breeding program, e.g., to increase seed, to introgress the novel construct into other lines or species, or for further selection of other desirable traits. Alternatively, transgenic plants can be obtained by vegetative propagation of a transformed plant cell, for those species amenable to such techniques.

Progeny of a transgenic plant are included within the scope of the invention, provided that such progeny exhibit altered oil content. Progeny of an instant plant include, for example, seeds formed on $F_1$, $F_2$, $F_3$, and subsequent generation plants, or seeds formed on $BC_1$, $BC_2$, $BC_3$, and subsequent generation plants.

Transgenic techniques for use in the invention include, without limitation, *Agrobacterium*-mediated transformation, electroporation, and particle gun transformation. Illustrative examples of transformation techniques are described in WO 99/43202 and U.S. Pat. No. 5,204,253 (particle gun) and U.S. Pat. No. 5,188,958 (*Agrobacterium*). Transformation methods utilizing the Ti and Ri plasmids of *Agrobacterium* spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art. In addition, various plant species can be transformed using the pollen tube pathway technique.

Nucleic acid constructs suitable for producing transgenic plants of the invention include a nucleic acid encoding a DAGAT polypeptide operably linked to a regulatory element such as a promoter. Standard molecular biology techniques can be used to generate nucleic acid constructs. To increase oil content in plants, the nucleic acid encoding a DAGAT polypeptide is operably linked to the regulatory element in sense orientation.

Suitable promoters can be constitutive or inducible, and can be seed-specific. As used herein, "constitutive promoter" refers to a promoter that facilitates the expression of a nucleic acid molecule without significant tissue- or temporal-specificity. An inducible promoter may be considered to be a "constitutive promoter", provided that once induced, expression of the nucleic acid molecule is relatively constant or uniform without significant tissue- or temporal-specificity. Suitable promoters are known (e.g., Weising et al., *Ann. Rev. Genetics* 22:421–478 (1988)). The following are representative examples of promoters suitable for use herein: regulatory sequences from fatty acid desaturase genes (e.g., *Brassica* fad2D or fad2F, see WO 00/07430); alcohol dehydrogenase promoter from corn; light inducible promoters such as the ribulose bisphosphate carboxylase (Rubisco) small subunit gene promoters from a variety of species; major chlorophyll a/b binding protein gene promoters; the 19S promoter of cauliflower mosaic virus (CaMV); as well as synthetic or other natural promoters that are either inducible or constitutive. In one embodiment, regulatory sequences are seed-specific, i.e., the particular gene product is preferentially expressed in developing seeds and expressed at low levels or not at all in the remaining tissues of the plant. Non-limiting examples of seed-specific promoters include napin, phaseolin, oleosin, and cruciferin promoters.

Additional regulatory elements may be useful in the nucleic acid constructs of the present invention, including, but not limited to, polyadenylation sequences, enhancers, introns, and the like. Such elements may not be necessary for expression of a DAGAT polypeptide, although they may increase expression by affecting transcription, stability of the mRNA, translational efficiency, or the like. Such elements can be included in a nucleic acid construct as desired to obtain optimal expression of the acyltransferase nucleic acid in the host cell(s). Sufficient expression, however, may sometimes be obtained without such additional elements. A reference describing specific regulatory elements is Weising et al., *Ann. Rev. Genetics* 22:421–478 (1988).

In some situations, a decreased oil content may be desired. A feature of the invention is that DAGAT activity can be reduced by gene silencing, antisense, ribozymes, cosuppression, or mutagenesis techniques, resulting in a decrease in oil content. Gene silencing techniques, such as that described in WO 98/36083 are useful. Antisense RNA has been used to inhibit plant target genes in a tissue-specific manner. See, for example, U.S. Pat. Nos. 5,453,566, 5,356,799, and 5,530,192. Antisense nucleic acid constructs include a partial or a full-length coding sequence operably linked to at least one suitable regulatory sequence in antisense orientation.

Expression of DAGAT also can be inhibited by ribozyme molecules designed to cleave DAGAT mRNA transcripts. While various ribozymes that cleave mRNA at site-specific recognition sequences can be used to destroy DAGAT mRNAs, hammerhead ribozymes are particularly useful. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is well known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., Proc. Natl. Acad. Sci. USA, 92(13):6175–6179 (1995); de Feyter, R. and Gaudron, J., Methods in Molecular Biology, Vol. 74, Chapter 43, "Expressing Ribozymes in Plants", Edited by Turner, P. C, Humana Press Inc., Totowa, N.J. (1997). RNA endoribonucleases such as the one that occurs naturally in *Tetrahymena thermophila*, and which have been described extensively by Cech and collaborators also are useful. See, for example, U.S. Pat. No. 4,987,071.

The phenomenon of co-suppression also has been used to inhibit plant target genes in a tissue-specific manner. Co-suppression of an endogenous gene using a full-length cDNA sequence as well as a partial cDNA sequence are known. See, for example, WO 94/11516, and U.S. Pat. Nos. 5,451,514 and 5,283,124. Co-suppression of DAGAT activity in plants can be achieved by expressing, in the sense orientation, the entire or partial coding sequence of a DAGAT gene.

Mutagenesis can also be used to reduce acytltransferase activity in plants. Mutagenic agents can be used to induce random genetic mutations within a population of seeds or regenerable plant tissue. Suitable mutagenic agents include, for example, ethyl methyl sulfonate, methyl N-nitrosoguanidine, ethidium bromide, diepoxybutane, x-rays, UV rays, and other mutagens known in the art. The treated population, or a subsequent generation of that population, is screened for reduced oil content or reduced DAGAT activity that results from the mutation. Mutations can be in any portion of a gene, including the coding region, introns, and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product.

Characterization of Oils

Techniques that are routinely practiced in the art can be used to extract, process, and analyze the oils produced by plants of the instant invention. Typically, plant seeds are cooked, pressed, and extracted to produce crude oil, which is then degummed, refined, bleached, and deodorized. Generally, techniques for crushing seed are known in the art. For example, soybean seeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

The majority of the seed oil can be released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures (i.e., degumming, caustic refining, bleaching, and deodorization). Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Deodorization can be performed by heating the oil to 500° F. (260° C.) under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum, e.g., in a Parr reactor and heated to 500° F. for the same length of time that it would have been deodorized. This treatment improves the color of the oil and removes a majority of the volatile substances.

Oil content can be measured by NMR using AOCS Method AM 2-93 and AOCS Recommended Practice AK 4–95 or by near infra-red reflectance spectroscopy (NIR) using AOCS Method AK 3-94 and AOCS Procedure AM 1-92. Oil composition can be analyzed by extracting fatty acids from bulk seed samples (e.g., at least 10 seeds). Fatty acid TAGs in the seed are hydrolyzed and converted to fatty acid methyl esters. Percentages of fatty acids typically are designated on a weight basis and refer to the percentage of the fatty acid methyl ester in comparison with the total fatty acid methyl esters in the sample being analyzed. Seeds having an altered fatty acid composition may be identified by techniques known to the skilled artisan, e.g., gas-liquid chromatography (GLC) analysis of a bulked seed sample, a single seed or a single half-seed. Half-seed analysis is well known in the art to be useful because the viability of the embryo is maintained and thus those seeds having what appears to be a desired fatty acid profile may be planted to form the next generation. However, bulk seed analysis typically yields a more accurate representation of the fatty acid profile of a given genotype. Fatty acid composition can also be determined on larger samples, e.g., oil obtained by pilot plant or commercial scale refining, bleaching and deodorizing of endogenous oil in the seeds.

The following examples are to be construed as merely illustrative of how one skilled in the art can make and use the DAGAT gene fragments, and does not limit the scope of the invention described in the claims.

EXAMPLES

Example 1

Cloning of a *Brassica* Acyl Transferase

A mouse acyl CoA:diacylglycerol acyltransferase (DAGAT) gene was recently identified (Case et al., *Proc Natl Acad Sci USA* 95:13018–13023, 1998). The deduced mouse DAGAT amino acid sequence was used to search for similar plant sequences in GenBank and dbEST databases. The mouse DAGAT protein sequence aligned with significant sequence identity and similarity to a putative *Arabidopsis thaliana* acyl-CoA:cholesterol acyltransferase (ACAT; GenBank Accession No. 3135276, locus ATAC003058). However, upon aligning the *A. thaliana* ACAT with the mouse DAGAT and mouse ACAT (Case et al., *J Biol Chem* 273:26755–26764, 1998) sequences, it was found that the *A. thaliana* protein had greater homology to mouse DAGAT than to mouse ACAT. Thus, the type of acyltransferase encoded by the *A. thaliana* gene was unclear.

The genomic DNA sequence encoding the *A. thaliana* protein (GenBank Accession No. 3135276) was used to design two PCR primers for amplifying candidate DAGAT or ACAT genomic sequences from different sources. The 5' DAGAT-1 primer had the sequence caucaucaucauACTGCCATGGACAGGTGTGATTCTGCTTTTTATCA (SEQ ID NO:1), and the 3' DAGAT-2 primer had the sequence cuacuacuacuaCTAGAGACAGGGCAATGTAGAAAGTATGTA (SEQ ID NO:2). Lowercase sequences were used for cloning into the pAMP1 vector (Gibco, BRL).

PCR amplification using DAGAT-1 and DAGAT-2 primers was carried out as follows. Each 100 µl PCR reaction mixture contained 50 ng of genomic DNA, 200 µM of each dNTP, 1×buffer B (Gibco BRL), 1 µM DAGAT-1 primer, 1 µM DAGAT-2 primer, 3 mM magnesium sulfate, and 2 µl Elongase enzyme (Gibco BRL). The reaction mixture was denatured at 94° C. for 3 minutes, followed by 30 cycles of denaturation at 94° C. for 1 minute, annealing at 50° C. for 2 minutes, and extension at 72° C. for 3 minutes. A final extension incubation was performed at 72° C. for 10 minutes after cycling. Based on the sequence of *A. thaliana* genomic DNA in GenBank Accession No. 3135276, a 1369 bp fragment was expected to be amplified from *Brassica*.

An approximately 1.4 kb fragment was amplified from genomic DNA isolated from *Brassica napus* variety Westar under PCR conditions described above. The amplified DNA fragment was cloned into the pAMP1 vector (Gibco BRL) and partially sequenced from the 5' end using a T7 universal primer and from the 3' end using a Sp6 universal primer. FIG. 1 contains a restriction map of the pAMP1 vector containing the putative DAGAT fragment, which has been designated pMB143. The partial sequence of the 5' end using the T7 primer was ATGGACAGGTGTGATTCTGCTTTTTATCAGGTGTCACGTTGATGCTCCTCACTTG CATTGTGTGGCTGAAGTTGGTTTCTTACGCTCATACTAACTATGACATAAGAACC CTAGCTAATTCATCTGATAAGGTAAAAGAAGTGATATAATATTGGTCACTTGCAT TGTGTTTTACTATTTTGACCAGACACTGTTGAAAACTGTAGGCCAATCCTGAAGT CTCCTACTATGTTAGCTTGAAGAGCTTGGCGTATTTCATGCTTGCTCCCACATTGT GTTATCAGGTAATCTGATGCGTCTTCTGCTAATTGTATCATACATTATCTTTCACT TGCAAAAGTTTCTTGTCTAAAACCTTGCGTCTTCGCTTTACCCAGCCGAGCTATCC ACGTTCT (SEQ ID NO:3).

The partial sequence of the 3' end using the Sp6 primer was ATCAATCTTGTCTTACTCAAAAATCATATTATGTTTACGTTANTAACCAAAATTC ATGTACGCACTGTCTACCTTTGTCAGTATTGGAGAATGTGGAATATGGTATGGTT CTCTTCTTGAACATCCCCTTCTTTTTTTATACAAAGCAGATTAAGAAAAGCTTATT GAGATCTTGTTTTTTCTAATAGCCTGTTCATAAATGGATGGTTCGACATGTATACT TTCCGTGCCTTCGCAGAAATATACCGAAAGTGAGTGTAGTTAATTGCGATGATCG ATATTTTTTTCTGTGCTTCATAAATTTAACCCTCCACTCATTTTTTTCCAGGTACCC GCTATTATCCTTGCTTTCTTAGTCTCTGCAGTCTTTCATGAGGTATAATACATACT TTCTACATTGNCCCTGTCTC (SEQ ID NO:4).

The sequence of the *B. napus* clone obtained using the T7 primer had an overall identity of 76.5% with the corresponding region of the *A. thaliana* gene, suggesting that the 1.4 kb cloned *B. napus* fragment encoded a protein that may be related to the *A. thaliana* DAGAT or ACAT.

Plasmid pMD143 was deposited with the American Type Culture Collection (ATCC), 10801 University Blvd. Manassas, Va. 20110–2209 on Jan. 15, 2003, under Accession No. PTA-4937.

Example 2

Reduction of Oil Content in *Brassica* Plants Expressing Antisense DAGAT

Figure 2:
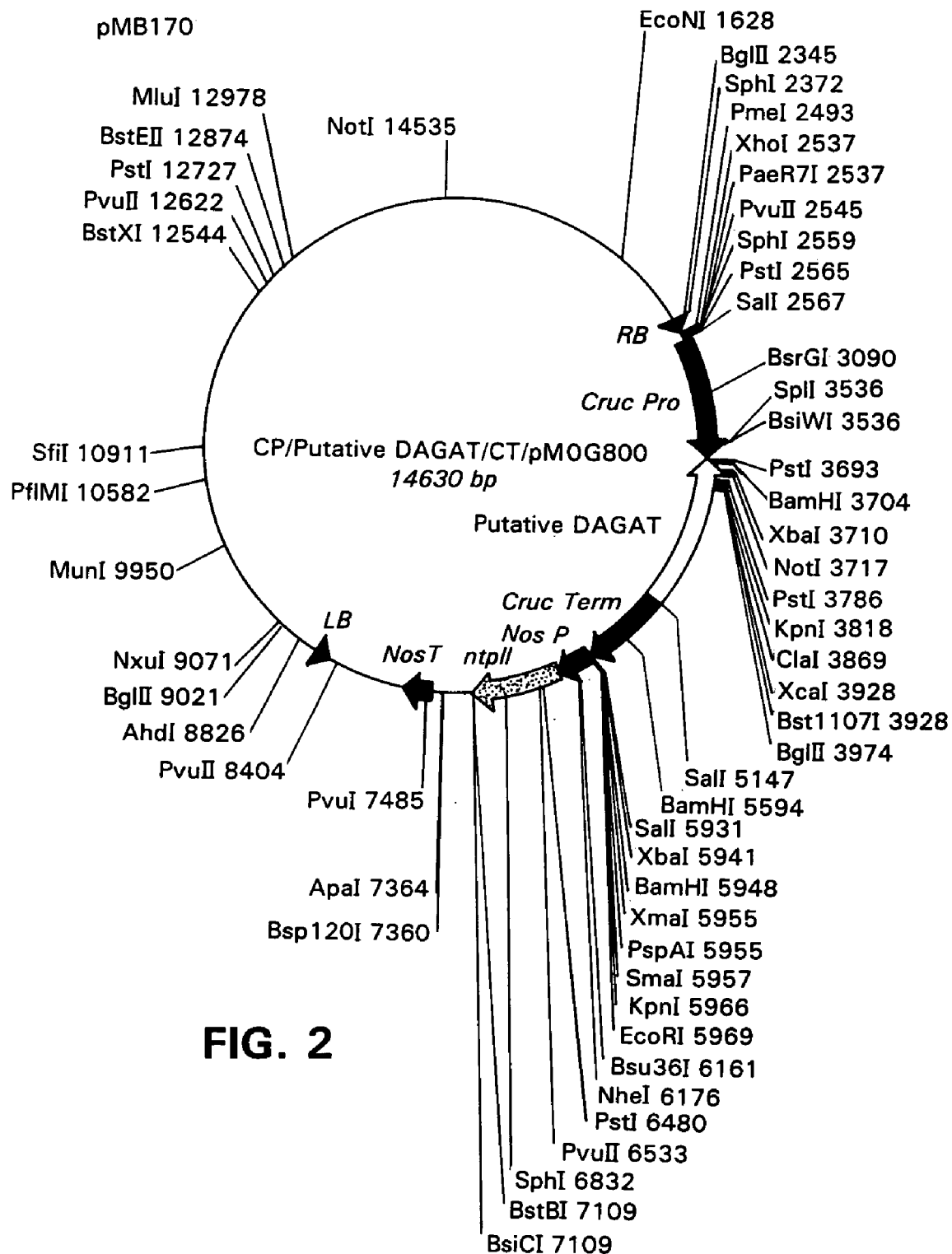
FIG. 2 is a schematic of a construct containing the acyltransferase in antisense orientation. Restriction sites are marked.

The putative DAGAT genomic DNA cloned in pAMP1 was excised with a SmaI/SnaBI digestion. The putative DAGAT fragment was purified and inserted at the blunted, EcoRI site of pMB 110 to generate pMB 171. This construct contains cruciferin promoter and cruciferin termination sequences. The antisense orientation of the putative DAGAT insert in pMB 171 was confirmed with restriction analysis. The cruciferin promoter/putative DAGAT/cruciferin termination cassette was released from pMB 171 by partially digesting with XbaI and completely digesting with XhoI, and cloned into the XhoI/XbaI sites of pMOG800 to generate pMB170. FIG. 2 provides a diagram of pMB170.

The construct pMB 170 was used to transform *Agrobacterium* LBA4404. The resulting *Agrobacterium* transformants were each co-cultivated separately with *B. napus* variety Westar hypocotyls and cultured consecutively on incubation, selection (containing kanamycin) and regeneration media until green shoots were produced. Regenerated plantlets were transferred to the greenhouse and grown to maturity. Each T1 plant (N=56) was selfed and the resulting T2 seeds were harvested from each individual T1 plant.

Oil, protein, chlorophyll, glucosinolate, oleic acid (18:1), linoleic acid (18:2), and α-linolenic acid (18:3) content were determined in the T2 seed samples. Oil content was measured by NIR using a Foss NIR Systems model 6500 Feed and Forage Analyzer (Foss North America, Eden Prairie, Minn.) calibrated according to manufacturer's recommendations. Canola seed samples, which represented wide ranges of the sample constituents listed above, were collected for calibration. Lab analysis results were determined using accepted methodology (i.e., oil, AOCS Method Ak 3-94; moisture, AOCS Method Ai 2-75; fatty acid, AOCS Method CE 1e-91 and AOCS Method CE 2-66; chlorophyll, AOCS Method CC 13D-55; protein, AOCS Method BA 4e-93; and glucosinolates, AOCS Method Ak 1-92). Instrument response also was measured for each sample. A calibration equation was calculated for each constituent by means of chemometrics. These equations are combined into one computer file and are used for prediction of the constituents contained in unknown canola samples.

T2 seed samples containing unknown levels of the above constituents were prepared by removing foreign material from the sample. Cleaned whole seed was placed into the instrument sample cell and the cell was placed into the instrument sample assembly. Analysis was carried out according to manufacturer instructions and was based on AOCS Procedure Am 1-92. The results are predicted and reported as % constituent (% oil and protein are reported based on dry weight). Conversion from 'dry weight' basis to 'as is' basis for oil and protein can be calculated using the following formula:

constituent (as is)=constituent (dry wt.)×[1−(% moisture/100)].

The average dried oil content of the T2 seeds (39.62±1.95%, n=56) was not significantly different from that of the control (Westar, 39.92±1.63, n—5). There were ten T1 plants, however, that produced T2 seeds having a lower total oil content. In these T2 seeds, the average oil content was 36.63±0.64%. Table 2 provides an analysis of eight of these 10 T2 seeds.

Approximately 10–20 T2 seeds from each of the ten selected plants were planted, and a nickel size portion of the leaf tissue was taken from plants about 2.5 weeks post-germination. Tissue samples were dried in a food dehydrator at 135° C. for 8–16 hours. DNA was isolated using the Qiagen Dneasy96 Plant Kit, and resuspended in 150 μl of buffer. PCR amplification was performed in a 20 μl volume containing 1×PCR buffer containing 1.5 mM $MgCl_2$ (Qiagen PCR Core Kit), 0.2 mM dNTP, 0.5 units Taq polymerase (Qiagen), 0.5 μM cruciferen primer (5'-CTT TAT GGA TGA GCT TGA TTG AG-3', SEQ ID NO:5), and 0.5 μM acyltransferase primer (5'-CCG CTC TAG AGG GAT CCA AGC-3', SEQ ID NO:6), 0.4% sucrose, and 0.008% cresol. Amplification conditions included 30 cycles of denaturation at 94° C. for 30 seconds, annealing at 55° C. for 30 seconds, and extension at 72° C. for 1 minute. PCR products were analyzed 1.2% agarose gel electrophoresis. As indicated in Table 1, the selected plants tested positive for the transgene.

TABLE 2

Analysis of T2 Seeds With Lower Oil Content

| SAMPLE | OIL | PROT | CHLOR | GLUC | C18:1 | C18:2 | C18:3 | (# pos. plants/ Total # plants tested) |
|---|---|---|---|---|---|---|---|---|
| Y350071 | 35.69 | 26.07 | 78.12 | 3.66 | 70.57 | 10.03 | 7.74 | 15/18 |
| Y350070 | 36.35 | 24.87 | 78.57 | 2.60 | 72.02 | 8.18 | 7.34 | 11/18 |
| Y350095 | 36.73 | 26.55 | 88.44 | 1.38 | 73.12 | 7.80 | 7.62 | 7/9 |
| Y350079 | 36.79 | 27.96 | 22.75 | 2.96 | 66.67 | 14.97 | 7.53 | 17/18 |
| Y350052 | 37.02 | 26.02 | 74.34 | 3.44 | 67.80 | 14.09 | 7.62 | 8/18 |
| Y350077 | 37.04 | 25.70 | 70.80 | 2.91 | 71.30 | 9.16 | 8.07 | 15/18 |
| Y350089 | 37.13 | 25.07 | 59.60 | 2.28 | 71.37 | 9.93 | 7.26 | 8/15 |
| Y350078 | 37.66 | 25.64 | 43.00 | 2.35 | 74.75 | 7.48 | 6.94 | 11/18 |
| Average | 36.80 | 25.99 | 64.45 | 2.70 | 70.95 | 10.23 | 7.51 | |
| Std Dev. | 0.58 | 0.97 | 21.79 | 0.72 | 2.65 | 2.81 | 0.34 | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid encoding a diacylglycerol acyltransferase polypeptide, wherein said nucleic acid is from the insert of pMB143, having American Type Culture Accession number PTA-4937.

2. An expression vector comprising said nucleic acid of claim 1 operably linked to an expression control element.

3. The expression vector of claim 2, wherein said expression control element is a constitutive promoter.

4. The expression vector of claim 2, wherein said expression control element is an inducible promoter.

5. The expression vector of claim 2, wherein said expression control element is a seed-specific promoter.

6. The expression vector of claim 5, wherein said seed-specific promoter is selected from the group consisting of the napin, phaseolin, oleosin, and cruciferin promoters.

7. The expression vector of claim 2, wherein said nucleic acid is operably linked to said expression control element in sense orientation.

8. A transgenic plant comprising said expression vector of claim 2.

9. The transgenic plant of claim 8, wherein said plant is a soybean plant.

10. The transgenic plant of claim 8, wherein said plant is a *Brassica* plant.

11. Seeds produced by said transgenic plant of claim 8.

12. Progeny of said transgenic plant of claim 8, wherein said progeny comprise said expression vector.

* * * * *

SEQUENCE LISTING

<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<223> OTHER INFORMATION: Synthetically generated primer

<400> SEQUENCE: 1
actgccatgg acaggtgtga ttctgctttt ttatca                36

<210> SEQ ID NO 2
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 2
ctagagacag ggcaatgtag aaagtatgta                                           30

<210> SEQ ID NO 3
<211> LENGTH: 396
<212> TYPE: DNA
<213> ORGANISM: Brassica napus

<400> SEQUENCE: 3
atggacaggt gtgattctgc ttttttatca ggtgtcacgt tgatgctcct cacttgcatt         60
gtgtggctga agttggtttc ttacgctcat actaactatg acataagaac cctagctaat        120
tcatctgata aggtaaaaga agtgatataa tattggtcac ttgcattgtg ttttactatt        180
ttgaccagac actgttgaaa actgtaggcc aatcctgaag tctcctacta tgttagcttg        240
aagagcttgg cgtatttcat gcttgctccc acattgtgtt atcaggtaat ctgatgcgtc        300
ttctgctaat tgtatcatac attatctttc acttgcaaaa gtttcttgtc taaaaccttg        360
cgtcttcgct ttacccagcc gagctatcca cgttct                                  396

<210> SEQ ID NO 4
<211> LENGTH: 410
<212> TYPE: DNA
<213> ORGANISM: Brassica napus
<220> FEATURE:
<221> NAME/KEY: misc_feature
<222> LOCATION: (1)...(410)
<223> OTHER INFORMATION: n = A,T,C or G

<400> SEQUENCE: 4
atcaatcttg tcttactcaa aaatcatatt atgtttacgt tantaaccaa aattcatgta         60
cgcactgtct acctttgtca gtattggaga atgtggaata tggtatggtt ctcttcttga        120 acatccccctt cttttttat acaaagcaga ttaagaaaag cttattgaga tcttgttttt        180
tctaatagcc tgttcataaa tggatggttc gacatgtata cttccgtgc cttcgcagaa         240 atataccgaa agtgagtgta gttaattgcg atgatcgata tttttttctg tgcttcataa        300 atttaacccct ccactcattt ttttccaggt acccgctatt atccttgctt tcttagtctc      360
tgcagtcttt catgaggtat aatacatact ttctacattg nccctgtctc                   410

<210> SEQ ID NO 5
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 5
ctttatggat gagcttgatt gag                                                 23

<210> SEQ ID NO 6
<211> LENGTH: 21
<212> TYPE: DNA
<213> ORGANISM: Artificial Sequence
<220> FEATURE:

-continued

```
<223> OTHER INFORMATION: Synthetically generated primer

<400> SEQUENCE: 6
ccgctctaga gggatccaag c                                              21
```